US011051533B2

(12) United States Patent
Lanter et al.

(10) Patent No.: US 11,051,533 B2
(45) Date of Patent: *Jul. 6, 2021

(54) GEL BASED LIVESTOCK FEED, METHOD OF MANUFACTURE AND USE

(71) Applicant: PURINA ANIMAL NUTRITION LLC, Arden Hills, MN (US)

(72) Inventors: Kent Lanter, Waterloo, IL (US); Brenda de Rodas, O'Fallon, MO (US); Bill L. Miller, Labadie, MO (US); Gary E. Fitzner, Stillwater, MN (US)

(73) Assignee: PURINA MILLS, LLC, Arden Hills, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/850,307

(22) Filed: Apr. 16, 2020

(65) Prior Publication Data

US 2020/0236972 A1 Jul. 30, 2020

Related U.S. Application Data

(60) Continuation of application No. 16/502,012, filed on Jul. 2, 2019, now Pat. No. 10,653,167, which is a continuation of application No. 16/255,136, filed on Jan. 23, 2019, now Pat. No. 10,383,346, which is a continuation of application No. 16/111,932, filed on Aug. 24, 2018, now Pat. No. 10,231,473, which is a continuation of application No. 15/894,125, filed on Feb. 12, 2018, now Pat. No. 10,085,466, which is a continuation of application No. 14/798,928, filed on Jul. 14, 2015, now Pat. No. 9,918,487, which is a continuation of application No. 13/096,437, filed on Apr. 28, 2011, now abandoned, which is a division of application No. 11/002,838, filed on Dec. 2, 2004, now Pat. No. 8,092,853.

(60) Provisional application No. 60/526,253, filed on Dec. 2, 2003.

(51) Int. Cl.
| | |
|---|---|
| *A23K 20/158* | (2016.01) |
| *A23K 20/163* | (2016.01) |
| *A23K 50/30* | (2016.01) |
| *A23K 20/24* | (2016.01) |

(52) U.S. Cl.
CPC .......... *A23K 20/158* (2016.05); *A23K 20/163* (2016.05); *A23K 20/24* (2016.05); *A23K 50/30* (2016.05); *Y10S 426/807* (2013.01)

(58) Field of Classification Search
CPC .... A23K 20/158; A23K 20/163; A23K 20/24; A23K 50/30; Y10S 426/807
See application file for complete search history.

(56) References Cited

U.S. PATENT DOCUMENTS

| | | |
|---|---|---|
| 1,549,196 A | 8/1925 | Burrows et al. |
| 2,400,834 A | 5/1946 | Le |
| 2,441,729 A | 5/1948 | Steiner |
| 2,918,375 A | 12/1959 | Gibsen |
| 3,349,079 A | 10/1967 | Freedman |
| 3,365,305 A | 1/1968 | Hunter |
| 3,401,039 A | 9/1968 | Gordon et al. |
| 3,438,780 A | 4/1969 | Singer |
| 3,455,701 A | 7/1969 | Miller et al. |
| 3,635,723 A | 1/1972 | Shelton et al. |
| 3,640,741 A | 2/1972 | Etes |
| 3,700,459 A | 10/1972 | Riley |
| 4,010,262 A | 3/1977 | Cardon et al. |
| 4,143,168 A | 3/1979 | Bernotavicz |
| 4,276,311 A | 6/1981 | Burrows et al. |
| 4,276,319 A | 6/1981 | Nguyen et al. |
| 4,283,400 A | 8/1981 | Von et al. |
| 4,293,576 A | 10/1981 | Sentence |
| 4,348,418 A | 9/1982 | Smith et al. |
| 4,423,083 A | 12/1983 | Shenouda |
| 4,436,759 A | 3/1984 | Trilling et al. |
| 4,560,570 A | 12/1985 | Rausing et al. |
| 4,603,054 A | 7/1986 | Schmidt et al. |
| 4,643,908 A | 2/1987 | Sawhill |
| 4,734,402 A | 3/1988 | Hashimoto et al. |
| 4,790,991 A | 12/1988 | Shaw et al. |
| 4,826,691 A | 5/1989 | Prochnow |
| 4,937,082 A | 6/1990 | Sawhill |
| 5,217,740 A | 6/1993 | Lanter |
| 5,413,802 A | 5/1995 | Baumanis et al. |
| 5,525,353 A | 6/1996 | Fajt |
| 5,596,084 A | 1/1997 | Sanderson et al. |
| 5,718,916 A | 2/1998 | Scherr |

(Continued)

FOREIGN PATENT DOCUMENTS

| | | |
|---|---|---|
| CA | 2133502 A1 | 4/1995 |
| EP | 0032304 A1 | 7/1981 |

(Continued)

OTHER PUBLICATIONS

"Alginates", Downloaded from www.fmcbiopolymer.com/othermarkets/OtherMarkets/ . . . /Alginate,cached, Jan. 2002, 1 page.

(Continued)

*Primary Examiner* — Walter A. Moore
(74) *Attorney, Agent, or Firm* — Dorsey & Whitney, LLP

(57) ABSTRACT

A method of making a gel-type livestock feed includes initially forming a feed mixture by mixing feed nutrient components, water, alginate, and a calcium component insoluble in water or a sequestrate to inhibit the calcium component from reacting with the alginate. Once the feed mixture is formed, the calcium component is solubilized or the sequestrates affecting the reactivity between the alginate and the calcium component is removed such that a gel feed is formed that includes a gel matrix containing the feed nutrient components. The gel feed may then be fed to the livestock. In another aspect of the present invention, piglets are weaned by feeding the gel feed for at least seven days directly after weaning. The gel feed may also include protein derived from blood with or without egg protein.

18 Claims, No Drawings

(56) References Cited

U.S. PATENT DOCUMENTS

| | | |
|---|---|---|
| 5,795,585 A | 8/1998 | Ikeda et al. |
| 5,928,686 A | 7/1999 | Ivey et al. |
| 6,004,576 A | 12/1999 | Weaver et al. |
| 6,009,657 A | 1/2000 | Morton et al. |
| 6,171,632 B1 | 1/2001 | Lanter et al. |
| 6,528,084 B2 | 3/2003 | Yu et al. |
| 6,534,104 B1 | 3/2003 | Derouchey et al. |
| 6,733,759 B2 | 5/2004 | Ivey et al. |
| 6,800,306 B1 | 10/2004 | Baekken et al. |
| 7,053,066 B2 | 5/2006 | Chawan |
| 10,383,346 B2 | 8/2019 | Lanter et al. |
| 2002/0039616 A1 | 4/2002 | Lanter et al. |
| 2002/0172737 A1 | 11/2002 | Pinski et al. |
| 2003/0072803 A1 | 4/2003 | Goldenberg et al. |
| 2003/0147992 A1 | 8/2003 | Lanter et al. |
| 2004/0058003 A1 | 3/2004 | Rosenberg et al. |
| 2004/0096440 A1 | 5/2004 | Weaver et al. |
| 2005/0238782 A1 | 10/2005 | Kelly et al. |
| 2019/0150480 A1 | 5/2019 | Lanter et al. |
| 2019/0320686 A1 | 10/2019 | Lanter et al. |

FOREIGN PATENT DOCUMENTS

| | | |
|---|---|---|
| EP | 0345886 A2 | 12/1989 |
| EP | 3542640 A1 | 9/2019 |
| FR | 1549196 A | 12/1968 |
| FR | 2343431 A1 | 10/1977 |
| FR | 2417947 A1 | 9/1979 |
| FR | 2522477 A1 | 9/1983 |
| FR | 2821245 A1 | 8/2002 |
| GB | 1153135 A | 5/1969 |
| GB | 1549196 A | 8/1979 |
| GB | 2149639 A | 6/1985 |
| JP | 1-41609 | 9/1989 |
| JP | H06245712 A | 9/1994 |
| JP | H06276961 A | 10/1994 |
| JP | H10127232 A | 5/1998 |
| JP | 2001008640 A | 1/2001 |
| JP | 2004528026 A | 9/2004 |
| SU | 725643 A1 | 4/1980 |
| WO | 9203938 A1 | 3/1992 |
| WO | 9511665 A1 | 5/1995 |
| WO | 9847392 A1 | 10/1998 |
| WO | 0101792 A1 | 1/2001 |
| WO | 0174176 A2 | 10/2001 |
| WO | 02076236 A1 | 10/2002 |
| WO | 03013717 A2 | 2/2003 |
| WO | 03030654 A1 | 4/2003 |
| WO | 03088767 A1 | 10/2003 |
| WO | 2007011330 A1 | 1/2007 |

OTHER PUBLICATIONS

"Fiber Content Chart", http://www.wehealnewyork.org/healthinfo/dietaryfiber/fibercontentchart.html, Jan. 2001, 8 pages.

"Mazuri Amphibian and Carnivorous Reptile Gel", Downloaded from www.mazuri.com, Jan. 2001, 2 pages.

"Mazuri Aquatic Gel Diet", Downloaded from www.mazuri.com, Jan. 2001, 2 pages.

"Nursery Phase: Nutrition and Diet Management Concepts", Nutrition vol. 3 No. 1; Downloaded from archived database http://www.pic.com, Apr. 2003.

CRC Press LLC, "Handbook for Food Additives", 2nd Edition; vol. 1; see particularly p. 301, 1973, 14 pages.

De Rodas, Brenda Z. et al., "Gel-based feed improves performance of nursery pigs", American Association of Swine Veterinarians, 2005, pp. 125-128.

EPO, "Letter of Opposition", App. No. 05772094.8, Jan. 7, 2016, 21 pages.

EPO, "Partial European Search Report", App. No. 05772094.8, Apr. 1, 2010, 13 pages.

EPO, "Summons to Attend Oral Proceedings", App. No. 05772094.8 (Pat. No. 1909594), Jan. 17, 2017, 7 pages.

EPO, "European Extended Search Report" Application No. 19173397.1, dated Aug. 23, 2019 10 pages.

Gombotz, et al., "Advanced Drug Delivery Reviews 31", 1998, pp. 267-285.

JPO, "Office Action—Purina Mills, LLC", App. No. 2008-521365, filed Jul. 14, 2005; Pub. No. 2009-501023, dated Jan. 30, 2013.

JPO, "Office Action—Purina Mills, LLC", App. No. 2012-086182, Filed Jul. 14, 2005; Pub. No. 2012-130355, dated Jan. 30, 2013.

Lewis, et al., "Feeding the Weaned Pig", Swine Nutrition 2nd Edition, 2001, pp. 704-715.

Lieberman, et al., "Pharmaceutical Dosage Forms: Disperse Systems", Published by Marcel Dekker, Inc. vol. 2, 1996, pp. 405-406.

Morris, et al., "J. Sci. Food. Agric.", vol. 35, 1984, pp. 1370-1376.

Phillips, G.O. et al., "Handbook of Hydrocolloids", Published by Woodhead, (CRC Press), 2000, pp. 379-395.

Stephen, Alistair A, "Food Polysaccharides and their applications", Published by Marcel Dekker, Inc. NY, 1995, p. 271.

U.S. Pat. No. 10,653,167, issued May 19, 2020.
U.S. Pat. No. 10,383,346, issued Aug. 20, 2019.
U.S. Pat. No. 10,231,473, issued Mar. 19, 2019.
U.S. Pat. No. 10,085,466, issued Oct. 2, 2018.
U.S. Pat. No. 9,918,487, issued Mar. 20, 2018.
U.S. Pat. No. 8,993,031, issued Mar. 31, 2015.
U.S. Appl. No. 13/096,437, filed Apr. 28, 2011.
U.S. Pat. No. 8,092,853, issued Jan. 10, 2012.

GEL BASED LIVESTOCK FEED, METHOD OF MANUFACTURE AND USE

CROSS REFERENCE TO RELATED APPLICATIONS

This application is a continuation of U.S. patent application Ser. No. 16/502,012 filed Jul. 2, 2019, mow U.S. Pat. No. 10,653,167, which is a continuation of U.S. patent application Ser. No. 16/255,136, filed Jan. 23, 2019, now U.S. Pat. No. 10,383,346, which is a continuation of U.S. patent application Ser. No. 16/111,932, filed Aug. 24, 2018, now U.S. Pat. No. 10,231,473, which is a continuation of U.S. patent application Ser. No. 15/894,125 filed Feb. 12, 2018, now U.S. Pat. No. 10,085,466, which is a continuation of U.S. patent application Ser. No. 14/798,928 filed Jul. 14, 2015, now U.S. Pat. No. 9,918,487, which is a continuation of U.S. patent application Ser. No. 13/096,437 filed Apr. 28, 2011, now abandoned, which is a divisional of U.S. patent application Ser. No. 11/002,838 filed Dec. 2, 2004, now U.S. Pat. No. 8,092,853, which claims the benefit of U.S. Provisional Patent Application Ser. No. 60/526,253 filed Dec. 2, 2003.

BACKGROUND OF THE INVENTION

The present invention includes a method of feeding livestock and in particular feeding swine. It also involves a novel composition of a gel feed and a method of manufacturing such a gel feed.

There are many situations in which a feed and a supply of water are both needed but are difficult to provide or providing both results in extra expense. For example, when livestock are being transported it is difficult and expensive to maintain a supply of water for such livestock. In addition, there are situations in the life of an animal where the animal has not much interest in consuming feed but has particular nutritional needs. For example, transitional stages such as weaning pose nutritional problems since the young animal has to learn how to consume solid food. It is sometimes difficult for the young animal to get accustomed to nourishment other than by suckling. Early weaning provides advantages relating to avoidance of diseases and increased weight gain. However, care is needed in early weaning to ensure that the young animal consumes sufficient nutrients.

Sows also require special nutritional needs just prior to and after farrowing. Proper nutrient intake is needed by the sow for the growth of developing fetuses, the sow's own body needs (body maintenance), for lactation and minimizing any feed intake depression by the sow after farrowing.

Growing and finishing pigs on occasion also have special nutrient requirements which may be due to any number of factors such as diseases and environmental factors. Diseases and environmental factors may affect nutritional intake which in turn have an affect on profitability for the swine farmer.

SUMMARY OF THE INVENTION

The present invention includes a method of making a gel-type feed for livestock. The method includes initially forming a feed mixture by mixing feed nutrient components, water, alginate, a calcium component insoluble in water or a sequestrate to inhibit the calcium component from reacting with the alginate. Once the feed mixture is formed, the calcium component is solubilized or the sequestrate's affect on the reactivity between the alginate and the calcium component is removed such that a gel feed is formed that includes a gel matrix containing the feed nutrient components.

The present invention also includes a method of feeding the gel feed to livestock made according to the method of this invention.

In another aspect of the present invention, piglets are weaned by feeding the gel feed containing the nutrients for at least seven days directly after weaning.

In yet another aspect of the present invention, the gel livestock feed includes an alginate based gel matrix in which water is the major component and protein derived from blood, such as plasma or serum. In another aspect, egg protein may be substituted or combined with the blood derived protein.

The present invention also includes a method of providing water to confined livestock by providing to the confined livestock its daily requirements of water by feeding the confined livestock a gel feed wherein water is the major component.

DETAILED DESCRIPTION OF THE PREFERRED EMBODIMENTS

The present invention provides a nutrient containing palatable shelf stable feed in a gel matrix whose major component is water. The gel feed provides livestock with both a feed component and a water component to an extent that no additional water external of the feed is needed for the livestock's sustenance. By livestock is meant agricultural or farm animals such as swine, horses, cattle, sheep or goats raised in a farm, ranch or agricultural setting or animals kept in zoos or zoological settings.

Alternatively, the gel may be used along without any nutrients solely as a water source. Providing water to swine that are confined such as being transported individually in pens or in a truck trailer without pens is difficult at best. Providing water in solid form eliminates spillage due to vehicle movement or animal collisions.

In addition, the gel feed of the present invention may be used as a delivery system for medication such as antibiotics and chemotherapeutics or for microbial supplements such as probiotics and nutraceuticals. When used as a delivery system for medication, the medication may be the sole constituent in the gel. Examples of antibiotics approved for swine include apramycin, bacitracin methylene disacylate, bacitracic zinc, bambermycins, chlortetracycline, lincomycin, neomycin, oxytetracycline, penicillin, tiamulin, tylosin, and virginiamycin. Chemotherapeutics approved for swine include arsanilic acid, carbodox, roxarsone, sulfamethazine and sulfathiazole. Other medication for swine are well known and are within the scope of the present invention.

The consistency of the gel-type feed of the present invention may range from a soft gel having the consistency of pudding to a harder gel having the consistency of a gel candy such as Gummy Bears®. The gel can be described as a hydrogel that is a colloidal gel in which water is a dispersion medium. One consideration in the consistency of the gel is that the gel not stick to the feeding animal. Gel that sticks to the swine poses two problems. The first problem relates to the cleanliness of the animal and to the pen in which the animal is contained. The other problem is waste of feed, since the animal cannot consume the feed that sticks to its face and other parts of the body that are not reachable by the animal's mouth. It is not very important as to how hard the gel is and in most situations, preferably the major component will be water. By major component is meant that the weight percent of water is higher than any other component in the gel feed.

The composition of the gel feed of the present invention is as follows:

TABLE 1

| Component | Approximate Weight Percent On a Wet Basis |
|---|---|
| Protein | 2-25 |
| Carbohydrate | 3-40 |
| Fat | 0-10 |
| Fiber | Less than 2 |
| Water | 25-90 |

Suitable sources for protein useful in the composition of the present invention include both animal and plant based protein. A non-exhaustive list of animal based protein includes meat meal, meat and bone meal, blood meal, red blood cells, dried porcine solubles, hydrolyzed feather meal, fish meal, dried milk, plasma and serum protein, poultry by-product meal, dried whey, whey protein concentrate and eggs. Suitable concentration of plasma and/or a serum protein in gel feed is about 0-25 wt. % and a suitable concentration of egg is about 0-15%. A non-exhaustive list of plant based protein includes alfalfa meal, canola seed meal, rice protein, coconut meal (copra), wheat gluten, potato protein, cotton seed meal, linseed meal (flax), peanut meal, safflower meal, sesame meal, soybean meal, soybean proteins and sunflower meal and other oil seed meals.

Sources for carbohydrates useful in the present invention include sorgum flour, ground rice, rice flour, ground corn, oat products, wheat, ground sorgum, or starch from any suitable grain such as wheat, oats, barley, and triticale, or tubers such as tapioca, and potato. Lactose, dextrin, sucrose, fructose and other simple sugars are also suitable carbohydrates.

Fat useful in the present invention may come from both plant or animal sources. Some fat may be the result of inclusion in the protein or carbohydrate source. However, additional fat may be added and is typically a rendered product such as a blended fat (animal and vegetable blends), or may be a poultry fat or tallow or a vegetable source such as soybean oil, corn oil, canola oil, coconut oil, olive oil and the like. Fat is necessary as a source of energy and also in the assimilation of certain vitamins that may be added to the feed of the present invention.

Fiber useful in the present invention is dietary fiber. Principal sources of dietary fiber are the same plant sources that provide protein and/or carbohydrates. If additional dietary fiber is needed, it may be obtained from such typical sources as soybean hulls or psyllium.

In addition to the nutrients discussed above, it may be desirable to provide additional supplementation of vitamins and minerals depending on the needs of the particular animal.

One gelling agent used in the present invention is a gum which binds with water and is capable of forming a matrix in which the feed components (nutrients discussed previously) are retained. Examples of suitable gums include agar, alginate, carrageenan, gum Arabic, ghatti, tragacanth, pectin, guar, Gelan, Carboxy Methylcellulose and locus bean. In the case of alginate, about 0.25 to 1.5 weight percent alginate of the feed components (excluding water) is necessary to form the gel. Other types of gels are also includable within the present invention, including those based on carbohydrates other than gums such as the starches including sorghum flour, ground rice, rice flour, ground extruded corn, ground sorghum, wheat and sugars including dextrin and sucrose. Other gelling agents that may be useful in the present invention include pectin, chitin, and gelatin based on animal protein.

The gel of the present invention is preferably a cold set gel, however, a gel made by heating the gum in water such as described in U.S. Pat. No. 5,217,740 which is hereby incorporated by reference is included within the present invention. In the specific embodiment discussed herein, the gel feed is not made through the use of an external heat source. Initially, the protein, carbohydrate, fat and fiber components and any other nutrients, vitamins, minerals or other supplements along with the gum and a source of calcium are mixed in water according to selected portions within the ranges of Table 1. The portions chosen are engineered for the particular animal and the particular period in the lifecycle of the animal. For example, piglets during and after weaning would require different portions of the components listed in Table 1 as compared to a sow during gestation.

Preferably, the source of calcium is insoluble with water or includes a sequestrant that inhibits the calcium from reacting with the alginate so that an immediate gel does not form. Gels formed through the reaction between calcium and alginate are well known. The propensity for alginate to form a gel and the difficulty of forming an appropriate gel are also well known. The method of the present invention in forming the gel provides for a controlled formation of alginate gel. The use of sequestrants or the use of acids to control alginate gel formation in the presence of calcium for use in human food is known.

Preferably, the source of calcium is a calcium salt which is initially insoluble but may be made soluble. One calcium salt suitable in the present invention is dicalcium phosphate. Dicalcium phosphate is virtually insoluble in water at a pH of 6 or above. Other calcium salts suitable for use include calcium carbonate, calcium gluconate, calcium iodate, calcium oxide, calcium sulfate.

Once the mixture is mixed, the pH is lowered. Preferably citric, fumaric, or propionic acid are used alone or in combination with other organic acids. Other organic or mineral acids or acidulents suitable in lowering the pH are included within the present invention. Once the pH is lowered below about pH 4.5, the gel of the present invention forms.

The strength of an alginate based gel depends on a number of factors including calcium levels, pH and the type of alginate used. Varying the calcium content, or varying the type of alginate used or adjusting the pH can create gels of different gel strength. Low calcium availability, either due to pH or low calcium concentration, may form a soft gel. A low pH may result in a harder gel. Water hardness may also have an effect on the formation of the alginate gel depending on the calcium carbonate content of the water.

The alginate based gel of the present invention may be made in either a batch or continuous manner. If made in a batch, the nutrients, alginate, dicalcium phosphate and water are mixed together. An organic acid is then added to lower pH to a selected level upon which the gel forms. However, mineral acids are also suitable for addition. For production in a continuous fashion, again a batch of nutrients with alginate, dicalcium phosphate and water are mixed initially in a tank. In a second tank, water and the acids are mixed.

These two mixtures are then pumped through an outlet line and mixed via an in line static mixer to continuously form the gel.

One particularly useful situation for the present invention includes providing nutrients to piglets during weaning. Weaning presents many challenges to the young pig. These challenges include an abrupt change from a liquid to a solid diet that contains ingredients that may not initially be easily digestible to the young pig. In addition, the young pig is presented with a new social structure. Combined, these effects disrupt nutrient intake that is necessary to maintain gut integrity. Such disruptions affect growth performance and are further exacerbated by an immature immune system which creates susceptibility to digestive upsets or diarrhea or both.

Research has shown that only 50% of the piglets drink water during the first 24 hours postweaning (Varley and Stockill, 2001).

During the first five days after weaning, water intake by the young pig fluctuates independently of apparent physiological need and water intake does not seem to be related to growth, feed intake or severity of diarrhea. (McLeese et al. 1992). After the fifth day, however, it seems that water intake follows a more consistent pattern that parallels growth and feed intake. It has been speculated that during the first few days after weaning, water consumption may be high as a consequence of a need for gut fill to obtain a sense of satiety in the absence of feed intake. Voluntary feed of early-weaned pigs fed dry diets during the first few days after weaning is often limited. Evidence suggests that growth rate of early-weaned pigs is largely limited by feed intake rather than growth potential. Pluske (1993) reported that the weanling pig does not meet the maintenance requirements until the 5$^{th}$ day after weaning at 21 days of age.

The gel product of the present invention provides the young piglet not only with the required nutrient intake but also with the appropriate water requirement. Utilizing the gel feed of the present invention, piglets surprisingly started eating the gel feed of the present invention almost immediately after weaning. Preferably, a gel-type feed for young piglets includes a high quality protein source such as spray dried plasma protein. It has been shown that spray dried plasma protein helps to improve performance during the first 7 to 14 days after weaning and during periods of stress for young pigs. It appears that plasma protein has biological functions beyond its nutritional qualities.

The present invention is more particularly described in the following examples that are intended as illustrations only since numerous modifications and variations within the scope of the present invention will be apparent to those skilled in the art.

Example 1

A total of 57 weaning pigs averaging 13.3 lb body weight were used in a 35-day growth trial. Some of the piglets were fed a gel based feed in which the gel matrix was a starch (Soft Set™ starch obtained from Staley Mfg. Co., of Decatur, Ill.). A control (no gel) feed along with two gel feeds, each gel feed containing a different protein source (Solutein™ or Appetein™ obtained from American Protein Corp of Ames, Iowa) were used in the trial. Appetein™ is a plasma based protein while Solutein™ is a serum based protein. The formulation for the gel containing Solutein™ is listed in Table 2 below while the gel containing Appetein™ is listed in Table 3 below.

TABLE 2

| Ingredient | Dry wt. % | Lbs. |
|---|---|---|
| Solutein ™ | 14.4000 | 1.44 |
| Sucrose | 19.6388 | 1.96 |
| Sodium Chloride | 0.4000 | 0.04 |
| Citric Acid Anhydrous | 2.0000 | 0.20 |
| Fumaric Acid | 4.0000 | 0.40 |
| Potassium Sorbate | 4.0000 | 0.40 |
| Propionic Acid | 2.0000 | 0.20 |
| Dicalcium Phosphate | 3.2000 | 0.32 |
| Choline Chloride 60% | 0.3897 | 0.04 |
| Luctarom LS$_1$ | 1.2000 | 0.12 |
| Soft Set Starch | 40.0000 | 4.00 |
| Mineral Pmx 2$_2$ | 2.3120 | 0.23 |
| Vit Pmx 1$_2$ | 3.3796 | 0.34 |
| Copper Sulfate | 0.0799 | 0.01 |
| Animal Fat | 3.0000 | 0.30 |

$_1$Lucta, S.A., Spain
$_2$Land O'Lakes, Inc., Arden Hills, MN

TABLE 3

| Ingredient | Dry wt. % | Lbs. |
|---|---|---|
| Plasma Protein (Appetein ™) | 14.4000 | 1.44 |
| Sucrose | 19.6388 | 1.96 |
| Sodium Chloride | 0.4000 | 0.04 |
| Citric Acid Anhydrous | 2.0000 | 0.20 |
| Fumaric Acid | 4.0000 | 0.40 |
| Potassium Sorbate | 4.0000 | 0.40 |
| Propionic Acid | 2.0000 | 0.20 |
| Dicalcium Phosphate | 3.2000 | 0.32 |
| Choline Chloride 60% | 0.3897 | 0.04 |
| Luctarom LS$_1$ | 1.2000 | 0.12 |
| Soft Set Starch | 40.0000 | 4.00 |
| Mineral Pmx 2$_2$ | 2.3120 | 0.23 |
| Vit Pmx 1$_2$ | 3.3796 | 0.34 |
| Copper Sulfate | 0.0799 | 0.01 |
| Animal Fat | 3.0000 | 030 |

$_1$Lucta, S.A., Spain
$_2$Land O'Lakes, Inc., Arden Hills, MN

The dry ingredients in the formulations listed in Tables 2 and 3 were blended in a 5-quart KitchenAid Mixer. Propionic acid and water (3 parts water to 1 part of the listed ingredients in Tables 2 and 3) were blended in five gallon buckets utilizing a Myers Mixer mixing the liquid contents for 30 seconds. After 30 seconds, the dry mix was added and the dry and liquid ingredient mixture were blended for an additional three minutes. Five batches of each formulation (Solutein™ and Appetein™) were made.

At weaning, pigs were sorted by weight, and divided into six weight groups (blocks). Dietary treatments were randomly assigned to pens (3-4 pigs per pen) within each of the weight groups (blocks, 6 replication/treatment). Pens within a block had the same number of pigs. Three dietary treatments were evaluated and consisted of the following:

TABLE 4

| TRT | 1 Control (no gel) | 2 Starch based gel with Solutein ™ | 3 Starch based gel with Appetein ™ (plasma protein) |
|---|---|---|---|
| Days 0-4 | | | |
| Pellet diet | Team Lean 10-15 | Team Lean 10-15 | Team Lean 10-15 |
| Gel type | None | Solutein ™ | Appetein ™ |

TABLE 4-continued

| TRT | 1<br>Control (no gel) | 2<br>Starch based gel<br>with Solutein ™ | 3<br>Starch based gel<br>with Appetein ™<br>(plasma protein) |
|---|---|---|---|
| Days 4-7 | | | |
| Pellet diet | Team Lean 10-15 | Team Lean 10-15 | Team Lean 10-15 |
| Gel type | None | 50:50 mix<br>(gel with<br>Solutein ™:<br>Team Lean 10-15) | 50:50 mix<br>(gel with<br>Appetein ™:<br>Team Lean 10-15) |

TABLE 4-continued

| TRT | 1<br>Control (no gel) | 2<br>Starch based gel<br>with Solutein ™ | 3<br>Starch based gel<br>with Appetein ™<br>(plasma protein) |
|---|---|---|---|
| Days 7-21 | | | |
| Pellet diet | Team Lean 14-20 | Team Lean 14-20 | Team Lean 14-20 |
| Days 21-35 | | | |
| Pellet diet | Team Lean 25-50 | Team Lean 25-50 | Team Lean 25-50 |

Team Lean 10-15 is a dry pelleted feed formulation from Purina Mills of St. Louis, MO.
Team Lean 14-20 is a dry pelleted feed formulation from Purina Mills of St. Louis, MO.
Team Lean 25-50 is a dry pelleted feed formulation from Purina Mills of St. Louis, MO.

Team Lean 10-15 pellets were fed for 7 days, Team Lean 14-20 pellets and Team Lean 25-50 pellets were fed for 14 days each. All pellets were fed in metal feeders attached to pen gates. Gel feeds were fed from days 0 to 4 postweaning in creep feeders, and a mix (50:50) of gel and dry feed (Team Lean 10-15 pellets) was fed from days 4 to 7 postweaning in creep feeders.

Pigs were housed in a conventional nursery facility in pens with a nipple waterer, four-hole feeder, and plastic grate flooring. Pigs had ad libitum access to feed and water. Pig body weight and feed intake (both gel feed and pellet) were determined at days 0, 4, 7, 14, 21, and 35 postweaning to evaluate average daily gain (ADG), average daily feed intake (ADFI), and feed:gain ratio. Gel feed intake was measured during the first week postweaning. In addition, fecal color and consistency scores were taken twice a week.

Data were analyzed as a randomized complete block design with pen as the experimental unit and blocks based on initial body weight. Mean separation for significant treatment effects was accomplished by least significant difference (LSD) procedures.

TABLE 5

| Gel Feed | TRT 1<br>None | TRT 2<br>with<br>Solutein ™ | TRT 3<br>with<br>Appetein ™ | SE | (1) | (2) | (3) |
|---|---|---|---|---|---|---|---|
| ADG Day 0-7 | 0.390 | 0.450 | 0.434 | 0.0988 | — | — | — |
| ADG Day 7-14 | 0.718 | 0.719 | 0.880 | 0.0709 | — | — | .14 |
| ADG Day 14-21 | 1.02$^a$ | 1.17$^b$ | 1.12$^b$ | 0.0288 | .01 | .01 | — |
| ADG Day 21-35 | 1.26 | 1.34 | 1.34 | 0.0335 | — | .10 | — |
| ADG 0-Final | 0.930 | 1.003 | 1.022 | 0.0388 | — | .11 | — |
| Dry gel intake | | | | | | | |
| Day 0 to 4, lb/hd/d | 0 | 0.169 | 0.154 | 0.0569 | — | .03 | — |
| Day 4 to 7, lb/hd/d | 0 | 0.090 | 0.071 | 0.0073 | .13 | .03 | — |
| Day 0 to 7, lb/hd/d | 0 | 0.135 | 0.119 | 0.0055 | .09 | .03 | |
| Pellets lb/hd/d, Day 0-7 | 0.43$^a$ | 0.647$^b$ | 0.627$^{ab}$ | 0.0636 | .07 | .03 | |
| ADFI Day 7-14 lb | 0.864 | 0.948 | 1.016 | 0.0819 | — | — | — |
| ADFI Day 14-21 lb | 1.22$^a$ | 1.38$^b$ | 1.39$^b$ | 0.0414 | .03 | .01 | — |
| ADFI Day 21-35 lb | 1.80 | 1.96 | 1.91 | 0.0585 | .20 | .09 | — |
| ADFI Day 0-35 lb | 1.22$^a$ | 1.40$^b$ | 1.40$^b$ | 0.0563 | .08 | .03 | |
| Gain/Feed Day 0-7 lb | 0.879 | 0.677 | 0.615 | 0.0883 | .14 | .06 | — |
| Gain/Feed Day 7-14 lb | 0.822 | 0.762 | 0.871 | 0.0582 | — | — | — |
| Gain/Feed Day 14-21 lb | 0.822 | 0.840 | 0.796 | 0.0148 | .17 | — | .07 |
| Gain/Feed Day 21-35 lb | 0.706 | 0.685 | 0.700 | 0.0147 | — | — | — |
| Gain/Feed Day 0-35 lb | 0.759 | 0.729 | 0.738 | 0.0121 | .20 | .10 | — |
| Initial Weight lb | 13.3 | 13.3 | 13.3 | 0.019 | — | — | — |
| 4 Day Weight lb | 14.4 | 14.7 | 14.9 | 0.369 | — | — | — |
| 7 Day Weight lb | 16.0 | 16.4 | 16.3 | 0.692 | — | — | — |
| 14 Day Weight lb | 21.0 | 21.5 | 22.5 | 1.00 | — | — | — |
| 21 Day Weight lb | 28.1 | 29.6 | 30.3 | 1.14 | — | — | — |
| 35 Day Weight lb | 45.8 | 48.4 | 49.1 | 1.37 | — | .11 | — |

PR > F if <.10 for (1) Geltype (2) Standard vs Gel (3) Solutein ™ vs Plasma
Values in treatment columns are simple arithmetic mean values and mean values in the same row not followed by a common letter differ (P < .05) using LSD procedure.

No significant differences (P≥0.1) were observed in ADG among treatment groups during days 0 to 7 and 7 to 14 postweaning (Table 5). Pigs fed gel feeds, however, had numerically greater ADO than pigs not fed gel feed. During days 14 to 21 and 21 to 35 postweaning, pigs fed the gel feeds continued to have greater (P<0.1) ADG than pigs receiving no gel feed. Similarly, during the overall 35 day trial period, pigs fed the gel feed tended to have greater (P<0.11) ADO than those not receiving the gel feeds. By day 35 postweaning, pigs fed the Solutein™ and Appetein™ containing gel were 2.6 and 3.3 lb heavier, respectively than those not receiving the gel feed.

Gel feed also containing Solutein™ intake was similar to gel feed containing Appetein™ intake during days 0 to 4, 4 to 7, and 0 to 7 postweaning. During days 0 to 7, ADFI of pellets was greater (P<0.03) in pigs fed the gel feed than in those not receiving the gel feed. This is probably an indication of some dry feed wastage when the pellets were mixed with the gel feed. During days 7 to 14, pigs fed the gel feed had numerically greater ADFI than those receiving no gel feed. During days 14 to 21, 21 to 35 and 0 to 35, pigs receiving the gel feed continued to have greater (P<0.1) ADFI.

During days 0 to 7 postweaning, pigs fed the gel feeds had lower (P<0.06) gain:feed ratio than those not receiving the gel feed. This is probably an indication of some dry feed wastage when the pellets were mixed with the gel feed. No significant differences were observed in gain:feed ratio among treatment groups during days 7 to 14, 14 to 21 and 21 to 35 postweaning.

No significant differences in fecal color score and consistency were observed among treatment groups.

The results of this trial indicate that feeding a gel feed containing Solutein™ or Appetein™ (plasma protein) during the first week after weaning improved performance of nursery pigs. Improvements in gain were more evident in later phases which may suggest that gel feed intake during the first week after weaning may have a carry-over effect through the rest of the nursery period. By the end of the trial, pigs fed the gel feed containing Solutein™ and plasma protein were 2.6 and 3.3 lb heavier, respectively, than those not receiving the gel feed.

Example 2

A total of 270 weaning pigs averaging 10.5 lb body weight were used in a 35-day growth trial. At weaning, pigs were sorted by weight, and divided into eleven weight groups (blocks). Each weight block had 20 or 25 piglets of as equal weight as possible. Five different dietary treatments were randomly assigned to each of the pens in each weight block. Each pen contained four or five piglets. The schedule of the dietary treatments is shown in Table 6 below:

TABLE 6

| Treatment Gel Type (day 0-7) | 1 None | 2 Alginate Based Gel with Solutein™ | 3 Alginate Based Gel with Plasma | 4 Alginate Based Gel with Plasma protein and egg | 5 Gel Based on 2 Alginate Types with Solutein™ |
|---|---|---|---|---|---|
| Dry Feed (pellets) | | | | | |
| Lean Metrics Infant[1] (I) (Day 0-7) | I | I | I | I | I |
| Lean Metrics Junior[1] (J) (Day 7-21) | J | J | J | J | J |
| Lean Metrics Senior[1] (S) (Day 21-35) | S | S | S | S | S |

[1]Dry feed pellets were produced at local feed mill and composition of pellets was according to Lean Metrics Starter Program of Purina Mills LLC. of St. Louis, MO.

The gel feeds for the four treatments in Table 6 above were mixed using a batch process. The composition of each of the treatments is indicated in Table 7 below. Initially, water, tetrasodium pyrophosphate, xanthan gum, alginate dicalcium phosphate and potassium sorbate were mixed together for about 2½ minutes in the proportions listed in Table 7 below. Treatment 5 (Table 6) utilized two alginate-types to form the gel. Then fat, vitamins and minerals, Luctarom®, and sucrose were mixed along with either dried animal plasma, Solutein™, or dried animal plasma and dried whole egg. The mixture was then mixed for one minute.

Each treatment was poured into five gallon buckets. While stirring the mixture in each of the five gallon buckets using a lab Myers mixer, fumaric acid, propionic acid and citric acid in the proportions listed in Table 7 were added until the mixture started to gel (about 15 seconds). Gel formation occurred in about five minutes.

TABLE 7

| Ingredient | Gel with Solutein™ | Gel with Plasma | Gel with Plasma Egg | Gel with 2 Alginate types with Solutein™ |
|---|---|---|---|---|
| LOL STARTER MINERAL PX[1] | 0.0525 | 0.0525 | 0.0525 | 0.0525 |
| LOL STARTER VITAMIN PX[1] | 0.0175 | 0.0175 | 0.0175 | 0.0175 |
| DRY LUCTAROM (FLAVOR)[2] | 0.075 | 0.075 | 0.075 | 0.075 |
| KELTROL-XANTHAN GUM[3] | 0.2 | 0.2 | 0.2 | 0.2 |
| CITRIC ACID ANHYDROUS | 0.5 | 0.5 | 0.5 | 0.5 |
| FUMARIC ACID | 1 | 1 | 1 | 1 |
| PROPIONIC ACID | 0.5 | 0.5 | 0.5 | 0.5 |
| MANUGEL GMB-ALGINATE[4] | 1 | 1 | 1 | 0.5 |
| MANUCOL DH-ALG1NATE[4] | — | — | — | 0.5 |
| OATMEAL | 10.84 | 9.4525 | 9.4525 | 10.84 |
| ANIMAL PLASMA-DRIED | — | 4.5 | 3 | — |
| DRIED WHOLE EGG | — | — | 1.5 | — |
| SOLUTEIN™ | 4 | — | — | 4 |
| DICALCIUM PHOSPHATE | 0.17 | 0.17 | 0.17 | 0.17 |
| SALT | 0.1 | 0.1 | 0.1 | 0.1 |
| SUCROSE | 4.7 | 5.5875 | 5.5875 | 4.7 |
| ANIMAL FAT | 0.75 | 0.75 | 0.75 | 0.75 |
| WATER | 75 | 75 | 75 | 75 |
| CHOLINE CHLORIDE 60% | 0.025 | 0.025 | 0.025 | 0.025 |
| COPPER SULFATE | 0.02 | 0.02 | 0.02 | 0.02 |
| POTASSIUM SORBATE | 1 | 1 | 1 | 1 |
| TETRASOD1UM PYROHOSPHATE | 0.05 | 0.05 | 0.05 | 0.05 |

[1]Land O'Lakes, Inc., Arden Hills, MN
[2]Lucta, S.A., Spain
[3]Monsanto Company, St. Louis, MO
[4]International Specialty Products, Wayne, New Jersey Pigs had ad libitum access to pelleted diets in metal feeders which were located on pen gates in each pen. Gel feeds for treatments 2, 3, 4 and 5 were fed in round pan type creep feeders added to each pen in which the piglets were to be subjected to a gel-type feed. The gel feed was fed ad libitum and gel feed was added later each day if all the gel feed in that pen was consumed. The piglets also had unlimited access to water. In treatments 2, 3, 4 and 5, dry feed (pellets) was added to the gel feed on days 3-7. On day 3, 0.1 pounds of dry feed was added per pound of gel feed. On day 4, 0.5 pounds of dry feed was added per pound of gel feed. On days 5, 6 and 7, 1 pound of dry feed was added per 1 pound of gel feed. Gel feed intake ended in all treatments after Day 7.

Pig body weight and feed intake (gel feed and pellet) were determined at initiation and days 7, 14, 21, and 35 postweaning to evaluate average daily gain (ADG), average daily feed intake (ADFI), and feed:gain ratio. In addition, fecal color and consistency scores were taken twice a week.

Data were analyzed as a randomized complete block design with pen as the experimental unit and blocks based on initial body weight. (See Table 8) The effects of initial weight (less than 10 lb and greater than 10 lb), gel type, and initial weight x gel type were evaluated.

intake during the first week after weaning had a carry-over effect through the rest of the nursery period. By the end of the trial, pigs weighing less than 10 lb and receiving the gel feed of treatments 2, 3, 4 and 5 were 3.44, 1.64, 3.83, and 4.17 lb, respectively heavier than pigs receiving no gel.

TABLE 8

|  | Less than 10 lb Body Weight | | | | | Greater than 10 lb Body Weight | | | | | SE | P > F if <.20 | | |
|---|---|---|---|---|---|---|---|---|---|---|---|---|---|---|
| Gel Type | None | Solutein | Plasma | Plasma and egg | Solutein and 2 alginates | None | Solutein | Plasma | Plasma and egg | Solutein and 2 alginates |  | Treat-ments[1] | Size v. treat-ment[2] | Gel Feed v. No Gel Feed[3] |
| Week 1 | | | | | | | | | | | | | | |
| ADG, lb | 0.202 | 0.285 | 0.201 | 0.318 | 0.235 | 0.391 | 0.360 | 0.338 | 0.388 | 0.325 | 0.020 | 0.04 | — | — |
| ADFI (pellet) only | 0.214 | 0.162 | 0.093 | 0.201 | 0.194 | 0.423 | 0.251 | 0.200 | 0.303 | 0.240 | 0.023 | 0.01 | 0.19 | 0.01 |
| Dry gel, lb | — | 0.170 | 0.200 | 0.184 | 0.146 | — | 0.188 | 0.233 | 0.183 | 0.179 | 0.017 | 0.05 | — | 0.01 |
| Wet gel, lb | — | 0.679 | 0.798 | 0.735 | 0.583 | — | 0.752 | 0.932 | 0.733 | 0.717 | 0.068 | 0.05 | — | 0.01 |
| Pellet in mix, lb | — | 0.294 | 0.315 | 0.306 | 0.241 | — | 0.303 | 0.318 | 0.299 | 0.299 | 0.0126 | 0.09 | — | 0.01 |
| Week 2 | | | | | | | | | | | | | | |
| ADG, lb | 0.321 | 0.318 | 0.322 | 0.358 | 0.391 | 0.582 | 0.567 | 0.509 | 0.587 | 0.508 | 0.0203 | — | 0.11 | — |
| ADFI (pellet) | 0.403 | 0.412 | 0.394 | 0.408 | 0.448 | 0.607 | 0.543 | 0.535 | 0.563 | 0.537 | 0.018 | — | — | — |
| Feed:gain | 1.274 | 1.298 | 1.279 | 1.162 | 1.153 | 1.045 | 0.971 | 1.066 | 0.973 | 1.076 | 0.038 | — | — | — |
| Week 3 | | | | | | | | | | | | | | |
| ADG, lb | 0.594 | 0.809 | 0.712 | 0.798 | 0.847 | 0.937 | 0.975 | 0.968 | 0.950 | 0.900 | 0.0357 | 0.12 | 0.07 | 0.01 |
| ADFI (pellet) | 0.742 | 0.914 | 0.821 | 0.897 | 0.954 | 1.173 | 1.171 | 1.086 | 1.101 | 1.079 | 0.029 | 0.18 | 0.02 | 0.18 |
| Feed:gain | 1.252 | 1.134 | 1.175 | 1.123 | 1.154 | 1.255 | 1.205 | 1.157 | 1.152 | 1.200 | 0.0423 | — | — | 0.06 |
| Weeks 3-5 | | | | | | | | | | | | | | |
| ADG, lb | 0.844 | 0.941 | 0.902 | 0.938 | 0.963 | 1.201 | 1.197 | 1.266 | 1.227 | 1.095 | 0.0342 | — | 0.13 | — |
| ADFI (pellet) | 1.091 | 1.261 | 1.175 | 1.237 | 1.257 | 1.624 | 1.587 | 1.664 | 1.626 | 1.439 | 0.036 | — | 0.01 | — |
| Feed:gain | 1.292 | 1.339 | 1.302 | 1.319 | 1.307 | 1.352 | 1.328 | 1.312 | 1.325 | 1.319 | 0.015 | — | — | — |
| Weeks 0-5 | | | | | | | | | | | | | | |
| ADG, lb | 0.561 | 0.659 | 0.608 | 0.670 | 0.680 | 0.863 | 0.859 | 0.869 | 0.876 | 0.784 | 0.0187 | 0.19 | 0.01 | 0.07 |
| ADFI (pellet) | 0.708 | 0.802 | 0.732 | 0.796 | 0.822 | 1.09 | 1.028 | 1.030 | 1.044 | 0.947 | 0.0201 | — | 0.01 | — |
| Feed:gain | 1.260 | 1.290 | 1.300 | 1.267 | 1.267 | 1.264 | 1.257 | 1.257 | 1.248 | 1.272 | 0.0131 | — | — | — |
| Pig Weight, lb | | | | | | | | | | | | | | |
| Initial | 8.51 | 8.52 | 8.51 | 8.52 | 8.52 | 12.13 | 12.14 | 12.14 | 12.13 | 12.14 | 0.002 | | | |
| Week 1 | 9.93 | 10.52 | 9.92 | 10.74 | 10.16 | 14.86 | 14.65 | 14.51 | 14.85 | 14.41 | 0.144 | 0.05 | — | — |
| Week 2 | 12.17 | 12.74 | 12.17 | 13.25 | 12.90 | 18.94 | 18.62 | 18.07 | 18.95 | 17.97 | 0.218 | 0.04 | 0.13 | — |
| Week 3 | 16.33 | 18.40 | 17.16 | 18.84 | 18.83 | 25.50 | 25.45 | 24.84 | 25.60 | 24.27 | 0.329 | 0.03 | 0.01 | 0.05 |
| Week 5 | 28.14 | 31.58 | 29.78 | 31.97 | 32.31 | 42.32 | 42.20 | 42.56 | 42.78 | 39.59 | 0.654 | 0.19 | 0.01 | 0.07 |

[1]Treatment effect
[2]Initial weight (greater than 10 lb versus less than 10 lb) x treatment interaction effect.
[3]No gel versus gel during the first week of treatment During the first week postweaning, numeric improvements in ADG were observed in pigs weighing initially less than 10 lb and fed a gel feed during the first week. No improvements in ADG, however, were observed in pigs weighing greater than 10 lb. During week 2, no significant differences were observed in ADG among treatment groups. During week 3, weeks 3-5, and during the overall 5-week trial period, a gel feed improved ADG of nursery pigs initially weighing less than 10 lb, but had little effect on pigs initially weighing greater than 10 lb at (initial wt×gel interaction, P=0.07, P=0.13, and P=0.01, respectively). Gel During the first week postweaning, pigs given gel feed consumed less (P<0.01) dry feed (pellets) than those not receiving the gel feed. Pigs receiving the gel feed with plasma consumed more gel feed but consumed less dry feed (pellets). Pigs receiving the 2 alginate-type gel feed with Solutein™ consumed less gel feed. No significant differences (P>0.1) were observed in ADFI among treatment groups during week 2.

A significant initial weight x gel type interaction (P<0.05) was observed in ADFI during week 3, weeks 3-5, and weeks 0-5. During week 3, pigs weighing <10 lb at weaning and receiving the gel containing Solutein™, plasma and egg, or the Solutein™ plus 2 alginates consumed more (P<0.05) dry feed (pellets) than those not receiving the gel feed. During weeks 3-5, pigs weighing <10 lb at weaning and receiving the Solutein™ or the Solutein™ plus 2 alginates gel consumed greater amounts (P<0.05) of dry feed than those receiving no gel. Pigs weighing >10 lb at weaning and receiving the Solutein™ plus 2 alginates gel consumed less (P<0.05) dry feed than those not receiving the gel. Similarly, during weeks 0-5, pigs weighing <10 lb at weaning and consuming the Solutein™, plasma plus egg or the Solutein™ plus 2 alginates gel consumed more dry feed (P<0.05) than those not receiving the gel. Pigs weighing >10 lb at weaning and fed the Solutein™ plus 2 alginates gel consumed less dry feed (P<0.05) than those fed the other treatments.

No significant differences were observed in feed:gain ratio among treatments during week 2, week 3, week 3-5, or weeks 0-5. During week 3, however, pigs fed gel feed during week 1 (treatments 2, 3, 4 and 5) had improved feed:gain compared to those receiving no gel feed (P<0.1).

The results of this trial indicate that feeding any of the gel feeds (treatments 2, 3, 4 and 5) during the first week after weaning improved performance of nursery pigs weighing less than 10 lb at weaning, but had little effect on performance of nursery pigs weighing greater than 10 lb at weaning. By the end of the trial (week 5), pigs weighing less than 10 lb at weaning and receiving gel feeds (treatments 2, 3, 4 and 5) were heavier than pigs receiving no gel feed. Pigs receiving the gel feed with plasma and egg had numerically greater gains than those fed treatments 2 and 3.

Example 3

One hundred-ninety weanling barrows (MCG GPK 35 maternal) averaging 12.2 lb body weight were used in a 35-day growth trial to evaluate the effect on performance of nursery pigs receiving a standard nursery program by feeding a gel feed during the first week after weaning. At weaning, pigs were sorted by weight, and divided into eight weight groups (blocks) of twenty or twenty five pigs per weight group. Four weight groups averaged 10.6 lb (small reps) and four weight groups averaged 13.8 lb (large reps). Pigs within each weight block were allotted into five equal subgroups (pens) of five or four pigs per pen (8 pens/ treatment; 4 small reps and 4 large reps/treatment). The number of pigs per pen within each block was kept constant. Dietary treatments were randomly assigned to pens (subgroups) within each of the weight groups (blocks). Five dietary treatments were evaluated during Phase 1 (day 1 to day 7 postweaning). Gels evaluated are described in the following table:

TABLE 9

| | Gel Type | | |
|---|---|---|---|
| Ingredient | Gel A 1% Algin, 75% H$_2$O | Gel B 0.5% Algin, 75% H$_2$O | Gel C 0.5 % Algin, 62% H$_2$O |
| LOL Starter Mineral PX[1] | 0.0525 | 0.0525 | 0.0525 |
| LOL Starter Vitamin PX[1] | 0.0175 | 0.0175 | 0.0175 |
| Dry Luctarom[2] | 0.075 | 0.075 | 0.075 |
| Keltrol-Xanthan Gum[3] | 0.2 | 0.2 | 0.0 |
| Citric Acid Anhydrous | 0.5 | 0.5 | 0.5 |
| Manugel GMB-Alginate[4] | 1 | 0.5 | 0.5 |
| Sodium Hexametaphosphate | 0.25 | 0.25 | 0.25 |
| Feeding Oatmeal | 9.2525 | 9.7525 | 14.09 |

TABLE 9-continued

| | Gel Type | | |
|---|---|---|---|
| Ingredient | Gel A 1% Algin, 75% H$_2$O | Gel B 0.5% Algin, 75% H$_2$O | Gel C 0.5 % Algin, 62% H$_2$O |
| Animal Plasma-Dried | 3 | 3 | 4.5 |
| Dried Whole Egg | 1.5 | 1.5 | 2.25 |
| Fructose | 0 | 5.5875 | 5.6 |
| Dicalcium Phosphate | 0.17 | 0.17 | 0.17 |
| Salt | 0.1 | 0.1 | 0.1 |
| Sucrose | 5.5875 | 0 | 5.6 |
| Animal Fat | 0.75 | 0.75 | 1.25 |
| Water | 75 | 75 | 62.5 |
| Choline Chloride 60% | 0.025 | 0.025 | 0.025 |
| Copper Sulfate | 0.02 | 0.02 | 0.02 |
| Fumaric Acid | 1 | 1 | 1 |
| Potassium Sorbate | 1 | 1 | 1 |
| Propionic Acid | 0.5 | 0.5 | 0.5 |

[1]Land O'Lakes, Inc., Arden Hills, MN
[2]Lucta, S.A., Spain
[3]Monsanto Company, St. Louis, MO
[4]International Specialty Products, Wayne, New Jersey The gel feeds described in Table 9 were mixed using the batch process as described in Example 2. The dry pelleted feeds, Lean Metrics Infant, Lean Metrics Junior, and Lean Metrics Senior are commercially available pelleted feed formulated for feeding to pigs according to their ages (days of treatment) described in Table 10.

TABLE 10

| | Treatment Description[a] | | | | |
|---|---|---|---|---|---|
| | Treatment 1 Control No Gel | Treatment 2 Gel A (75% H$_2$O) Plasma + egg 1% Algin (7 days) | Treatment 3 Gel B (75% H$_2$O) Plasma + egg 0.5% Algin (7 days) | Treatment 4 Gel C (62% H$_2$O) Plasma + egg 0.5% Algin (7 days) | Treatment 5 Gel A (75% H$_2$O) Plasma + egg 1% Algin (3 days) |
| Days 1-7 | | | | | |
| Pellets: Lean Metrics Infant (I) | I | I | I | I | I |
| Days 7-21 | | | | | |
| Pellets: Lean Metrics Junior (J) | J | J | J | J | J |
| Days 21-35 | | | | | |
| Pellets: Lean Metrics Senior (S) | S | S | S | S | S |

[a]Lean Metrics Infant, Lean Metrics Junior, and Lean Metrics Senior are dry pelleted feed formulations from Purina Mills, LLC of St. Louis, MO.

Pigs had ad libitum access to pelleted diets in metal feeders which were located on pen gates on treatments 1 to 4. Gel diets were fed in round creep feeders (added to each pen) to pigs on treatments 2, 3 and 4 on days 1 to 3 post weaning. On days 4-7, a combination of gel plus dry feed was offered in creep feeders to pigs in treatments 2-4. 0.1, 0.5, 1 and 1 lb of dry feed per lb of gel was added to the creep feeders on days 4, 5, 6, and 7, respectively. Pigs on treatment 5 were fed gel only in the metal feeders on the pen gates on days 1 to 2. On day 3, 1 lb of dry feed per lb of gel was added and offered in the metal feeder on the pen gate. On day 4 through the remainder of the study only dry feed was offered in the metal feeder on the pen gate.

Pig body weight and feed intake (pellet) were determined at initiation, days 7, 14, 21, and 35 post weaning to evaluate average daily gain (ADG), average daily feed intake (ADFI), and feed:gain ratio. Gel intake was measured during the first week post weaning. In addition, fecal color and consistency scores were taken twice a week.

Data was analyzed as a randomized complete block design with the pen as the experimental unit and block based on initial body weight. The effects of initial weight (small and large), rep (size), gel type, and initial weight x gel type were evaluated.

During the first week postweaning, no significant differences (P>0.10) were observed in ADG among treatment groups. Numeric improvements, however, were observed in ADG by supplementing the gel to weanling pigs. The greatest effect was observed with the smallest pigs. Pigs weighing less than 10.6 lb on average (9 to 12 lb) and fed the gel containing 75% water and 0.5% alginate (treatment 3) had numerically greater ADG than pigs fed the gel containing 62% water and 0.5% algin (treatment 4). The biggest pigs (weighing 13.8 lb on average, 12 to 17 lb), however, grew better when fed the gel containing 62% water than when fed the gel containing 75% water. In addition, pigs offered the gel in the regular feeders for the first three days after weaning had numerically greater ADG than those offered the gel in the creep feeders. This was probably due to greater consumption of dry feed by pigs offered the gel in the regular feeder for only three days and then followed by just dry feed in the regular feeders.

During week 2, week 3, and overall, the smallest pigs supplemented with the gel continued to have numerically greater ADO than those not supplemented with the gel. By day 35 postweaning, the smallest pigs on treatment 2, 3, 4, and 5 were 0.86, 1.53, 2.01, and 3.43 lb heavier, respectively than those no receiving the gel (treatment 1).

As expected, during week 1, pigs on treatment 5 (received gel for only 3 days) consumed less gel (P<0.05) but consumed more dry feed from the regular feeder (P<0.05) than pigs on treatment 2, 3, and 4. Pigs on treatment 5 consumed similar amounts of dry feed as those on treatment 1 (control). Pigs on treatment 2, 3, and 4 had greater pellet intake per day than those in treatment 1 or treatment 5. This may be a reflection of some feed wastage when pellets were mixed with the gel since pellet intake per day from the regular feeder was lower (P<0.05) in pigs fed treatment 2, 3, and 4 compared with pellet intake of pigs on treatment 1 and 5. During week 2, the smallest pigs receiving the gel had numerically greater (no statistically significant) pellet intake than those not receiving the gel.

During the first week postweaning, pigs on treatment 2, 3, and 4 had greater (P<0.05) feed:gain ratio than pigs on treatment 1 or treatment 5. This is probably an indication of feed wastage when the pellets were mixed with gel. During week 2, pigs in treatment 5 utilized feed more efficiently than those in treatment 2. No significant differences (P>0.1) were observed in feed:gain ratio during week 3 or week 3 to 5 among treatment groups.

The results of this study indicate that feeding a gel containing plasma and egg during the first week after weaning improved performance of nursery pigs weighing between 9 to 12 lb at weaning, but had little effect on performance of nursery pigs weighing between 12 to 17 lb at weaning. Similar to previous experiments, gel supplementation during the first week after weaning had a carry-over effect through the rest of the nursery period and had the greatest effect in the smallest reps of pigs. By day 35 postweaning, the smallest reps of pigs on treatment 2 (plasma:egg gel with 75% water and 1% alginate), treatment 3 (plasma:egg gel with 75% water and 0.5% algin), treatment 4 (plasma:egg gel with 62% water and 0.5% alginate), and treatment 5 (as treatment 2, but gel was offered in regular feeder for only 3 day) were 0.86, 1.53, 2.01, and 3.43 lb heavier, respectively than those no receiving the gel (treatment 1).

Example 4

Fifty four weanling pigs (MCG) averaging 7.5 lb bodyweight were used in a 40-day growth trial to evaluate the effect of feeding a gel with or without flavor on performance of nursery pigs receiving a standard nursery feeding program. At weaning, pigs were sorted by weight, and divided into six weight groups (blocks) of nine pigs per weight group. Dietary treatments were randomly assigned to pens (subgroups) within each of the weight groups (blocks). Three dietary treatments were evaluated during Phase 1 (day 1 to day 7 postweaning): 1) control (no gel), 2) a gel containing flavor, and 3) a gel without flavor.

The gel feeds (plasma and egg) were mixed using the batch process as described in Example 2. The dry pelleted feeds, Lean Metrics Premier, Lean Metrics Infant, Lean Metrics Junior, and Lean Metrics Senior are commercially available pelleted feed formulated for feeding to pigs according to their ages, (days of treatment) described in Table 11.

TABLE 11

| Treatment Description[a] | | | |
|---|---|---|---|
| | Treatment 1 Control No Gel | Treatment 2 Gel with flavor | Treatment 3 Gel without flavor |
| Days 1-7 | | | |
| Pellets: Lean Metrics Premier (P) | P | P | P |
| Days 7-14 | | | |
| Pellets: Lean Metrics Infant (I) | I | I | I |
| Days 14-28 | | | |
| Pellets: Lean Metrics Junior (J) | J | J | J |
| Days 28-40 | | | |
| Pellets: Lean Metrics Senior (S) | S | S | S |

[a]Lean Metrics Premier, Lean Metrics Infant, Lean Metrics Junior, and Lean Metrics Senior are dry pelleted feed formulations from Purina Mills, LLC of St. Louis, MO.

Pigs had ad libitum access to pelleted diets in metal feeders which were located on pen gates. Gel diets were fed in round creep feeders (added to each pen) to pigs on treatments 2 and 3 on days 1 to 3 post weaning. On days 4-7, a combination of gel plus dry feed was offered in creep feeders to pigs in treatments 2 and 3. 0.1, 0.5, 1 and 1 lb of dry feed per lb of gel was added to the creep feeders on days 4, 5, 6, and 7 respectively. Pig body weight and feed intake (pellet) were determined at initiation, days 7, 14, 28, and 40 post weaning to evaluate average daily gain (ADG), average daily feed intake (ADFI), and feed:gain ratio. Gel intake was measured during the first week post weaning.

Data was analyzed as a randomized complete block design with the pen as the experimental unit and block based on initial body weight.

During the first week postweaning, pigs fed the gel with or without flavor had greater (P<0.05) ADG than pigs not receiving gel, and pigs fed the gel with flavor had greater ADG than those fed the gel without flavor. Pigs fed the gel with flavor consumed greater amounts of gel than those fed the gel without flavor. Similarly, pigs fed the gels had numerically greater pellet intake than those not receiving the gel. By day 40 postweaning, pigs on treatment 2 (gel with flavor) and treatment 3 (gel without flavor) were 2.1 and 1.8 lb heavier, respectively than those not receiving the gel (treatment 1; Table 12).

TABLE 12

Performance of pigs fed a gel with our without flavor[a]

|  | Control | Gel with Flav | Gel without Flav | SEM |
|---|---|---|---|---|
| Day 0 to 40 |  |  |  |  |
| ADG, lb | 0.857 | 0.906 | 0.898 | 0.026 |
| Pellet intake, lb per day | 1.07 | 1.10 | 1.15 | 0.034 |
| Gel intake, lb per day | 0 | 0.328 | 0.185 | 0.043 |
| Initial Weight | 7.54 | 7.55 | 7.54 | 0.01 |
| Weight day 40 | 41.7 | 43.8 | 43.5 | 1.06 |

[a]Six pens per treatment and 3 pigs per pen (5.8-9.7 lb beginning weight, 9 to 14 day of age).

Example 5

A trial was conducted to evaluate the effect of feeding a gel (plasma and egg) three days prior to weaning and seven days postweaning on performance of nursery pigs. Ten litters received the gel in the farrowing crate on creep feeders or in a matt for 3 days prior to weaning. At weaning, ⅓ of each litter received the feeding program described in Table 13 for treatment 1, ⅓ received the feeding program described for treatment 2, and ⅓ received the feeding program described for treatment 3. A total of 90 weanling pigs averaging 10.9 lb were used. Only pigs in treatment 3 received gel in the nursery and were fed in round pan type creep feeders added to each pen. On day 4, 0.5 pounds of dry feed per pound of gel was added. On days 5, 6, and 7, 1 pound of dry feed per pound of gel was added.

The gel feeds (plasma and egg) were mixed using the batch process as described in Example 2. The dry pellet feeds are commercially available pellet feed formulated for feeding to pigs according to their ages (days of treatment) as described in Table 13.

TABLE 13

(Ration Use)[a]

| Treatment | 1 | 2 | 3 |
|---|---|---|---|
| Gel in Farrowing | Gel (plasma + egg) | Gel (plasma + egg) | Gel (plasma + egg) |
| Gel in Nursery (day 1-7) | No gel | No gel | Gel (plasma + egg) |
| Dry Diets | TW Program | UC Program | UC Program |
| Day 1-7 | UWP | UC200 | UC200 |
| Day 7-14 | LWT | UC240 | UC240 |
| Day 14-28 | TWPH2 | UC400 | UC400 |
| Day 28-39 | TWPH3 | UC500 | UC500 |

[a]Ultra Wean Plus (UWP), Litter Wean Transition (LWT), Top Wean Phase 2 (TWPH2), Top Wean Phase 3 (TWPH3), Ultra Care 200 (UC200), Ultra Care 240 (UC240), Ultra Care 400 (UC400), and Ultra Care 500 (UC500) are dry pelleted feed formulations from Land O'Lakes Farmland Feed, LLC.

Data was analyzed as a randomized complete block design with the pen as the experimental unit and block based on initial body weight.

During the first week postweaning, pigs fed the gel three days prior to weaning (farrowing crates) and in the nursery (treatment 3) had greater (P<0.05) ADG than pigs receiving the gel only in the farrowing crate (no gel in the nursery, treatment 1 and treatment 2). During day 0 to 28 postweaning, pigs receiving treatment 3 continued to have greater ADG (P<0.10) and ADFI (P<0.05) than pigs receiving dietary treatment 2 (Table 14). During the overall 39-day trial, pigs receiving treatment 3 had greater ADFI (P<0.05) than those receiving treatment 2.

TABLE 14

Performance per day 0 to 39 Postweaning[a]

|  | Top Wean | Ultra Care | Ultra Care + gel | SEM |
|---|---|---|---|---|
| Day 0 to 28 |  |  |  |  |
| ADG, lb per day | 0.894[de] | 0.866[d] | 0.912[e] | 0.015 |
| ADFI, lb per day | 1.05[bc] | 0.98[d] | 1.13[c] | 0.02 |
| Day 0 to 39 |  |  |  |  |
| ADG, lb per day | 1.02 | 1.03 | 1.06 | 0.018 |
| ADFI, lb per day | 1.29[b] | 1.27[b] | 1.38[c] | 0.015 |
| Pig weight, lb |  |  |  |  |
| Initial | 11.03 | 10.94 | 10.95 | 0.05 |
| Day 7 | 13.73[b] | 13.56[b] | 14.28[c] | 0.16 |
| Day 28 | 36.00[de] | 35.2[d] | 36.5[e] | 0.44 |
| Day 39 | 50.8 | 51.3 | 52.1 | 0.71 |

[a]Six pens per treatment and 5 pigs per pen (10.9 lb beginning weight).
[bc]Means in the same row with different superscript differ (P < 0.05)
[de]Means in the same row with different superscript differ (P < 0.10)

What is claimed is:

1. A method of making a livestock feed for piglets, the method comprising:
   forming a feed mixture by mixing feed nutrient components, a gelling agent, and a calcium salt which is initially insoluble in water but may be made soluble, wherein the gelling agent is a gum selected from the group consisting of alginate, carrageenan, gellan and pectin, and wherein during the step of forming the feed mixture the gelling agent does not react with the calcium salt; and
   once the feed mixture is formed, causing the gelling agent and the calcium salt to react such that a gel feed is formed comprising a gel matrix in which the feed nutrient components are retained,
   wherein the feed nutrient components comprise about 2 to 25% protein, about 3 to 40% carbohydrate, and about 0 to 10% fat.

2. The method of claim 1, wherein causing the gelling agent and the calcium salt to react involves adding an acid to the feed mixture to lower a pH of the feed mixture.

3. The method of claim 2, wherein the acid comprises citric acid, fumaric acid, propionic acid or any combination thereof.

4. The method of claim 2, wherein sufficient acid is added to lower the pH to at least about 4.5 or below.

5. The method of claim 1, wherein the calcium salt comprises dicalcium phosphate, calcium carbonate, calcium gluconate, calcium iodate, calcium sulfate or any combination thereof.

6. The method of claim 5, wherein the calcium salt becomes soluble and reactive with the gelling agent at a selected pH and the pH of the feed mixture is lowered to or below the selected pH.

7. The method of claim 1, wherein the feed nutrient components include water as a major component.

8. The method of claim 1, wherein the feed nutrient components comprise about 25 to 90% water.

9. The method of claim 1, wherein forming the feed mixture comprises adding antibiotics or chemotherapeutics.

10. The method of claim 1, wherein the protein comprises protein derived from an animal, a plant or a combination thereof.

11. The method of claim 1, wherein the gel feed is then fed to piglets during weaning, immediately after weaning or both.

12. A method of making a livestock feed for piglets, the method comprising:

forming a feed mixture by mixing feed nutrient components, a gelling agent, and a calcium salt which is initially insoluble in water but may be made soluble, wherein the gelling agent is a gum selected from the group consisting of alginate, carrageenan, gellan and pectin, and wherein the pH during mixing of the feed nutrient components is 6.0 or greater; and once the feed mixture is formed, lowering the pH to solubilize the calcium salt such that the gelling agent reacts with the solubilized calcium salt and a gel feed is formed comprising a gel matrix in which the feed nutrient components are retained, wherein the water is a major component of the gel matrix, and wherein the feed nutrient components comprise about 2 to 25% protein, about 3 to 40% carbohydrate, and about 0 to 10% fat.

13. The method of claim 12, wherein the calcium salt comprises dicalcium phosphate, calcium carbonate, calcium gluconate, calcium iodate, calcium sulfate or any combination thereof.

14. The method of claim 12, wherein the pH is lowered to at least about 4.5 or below to solubilize the calcium salt.

15. The method of claim 12, wherein the gel feed is then fed to piglets.

16. The method of claim 12, wherein forming the feed mixture comprises adding antibiotics or chemotherapeutics.

17. The method of claim 12, wherein the feed nutrient components comprise a protein derived from an animal, a plant or a combination thereof.

18. The method of claim 12, wherein the gel matrix comprises about 25 to 90% water.

* * * * *